United States Patent
Kumamoto et al.

(10) Patent No.: US 6,828,461 B2
(45) Date of Patent: Dec. 7, 2004

(54) PROCESS FOR PRODUCING 1,5-DIAMINONAPHTHALENE

(75) Inventors: Yukihiro Kumamoto, Fukuoka (JP); Masazumi Takaoka, Fukuoka (JP); Hideki Mizuta, Fukuoka (JP); Yoriaki Matsuzaki, Fukuoka (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/754,696

(22) Filed: Jan. 12, 2004

(65) Prior Publication Data

US 2004/0143137 A1 Jul. 22, 2004

Related U.S. Application Data

(63) Continuation of application No. PCT/JP03/14932, filed on Nov. 21, 2003.

(30) Foreign Application Priority Data

Dec. 4, 2002 (JP) ........................................ 2002-352642

(51) Int. Cl.$^7$ ...................... C07C 211/50; C07C 211/51
(52) U.S. Cl. ........................................................ 564/308
(58) Field of Search ......................................... 564/308

(56) References Cited

U.S. PATENT DOCUMENTS 4,973,758 A * 11/1990 Behre et al. ................. 564/394
6,737,548 B2 * 5/2004 Inoki et al. .................. 564/308

2002/0103401 A1 8/2002 Schelhaas et al.

FOREIGN PATENT DOCUMENTS

| DE | 397150 | 6/1924 |
| DE | 408665 | 1/1925 |

OTHER PUBLICATIONS

Database CAPLUS on STN, Acc. No. 2002:25852, Kanbara et al., JP 2002003452 (Jan. 9, 2002) (abstract).*
Rodriguez et al., Tetrahedron Letters, 2003 pp. 2691–2693, vol. 44 (Abstract).
Hamada et al., Nippon Kagaku Kaishi, 1983, pp. 420–427, No. 3 (Abstract).
Abstract of WO02/090315, Nov. 14, 2002.
Abstract of JP4–154745, May 27, 1992.
Abstract of JP7–278066, Oct. 24, 1995.
Hirashima et al., "Reduction of Aromtic Nitro Compounds with Hydarazine (Part 2)—Active Carbon–Iron(III) Chloride Catalyst", Nippon Kagkau Kaishi, 1975, No. 7, p. 1223 (Abstract).

* cited by examiner

*Primary Examiner*—Brian J. Davis
(74) *Attorney, Agent, or Firm*—Burns, Doane, Swecker & Mathis, L.L.P.

(57) ABSTRACT

A process for producing 1,5-diaminonaphthalene without formation of 1,8-diaminonaphthalene and not through an unstable nitro imine and nitro enamine as intermediates, the process including the steps of dehydrogenating 5-substituted-1-tetralone to produce a naphtol compound and then aminating the hydroxyl group of the naphtol compound.

6 Claims, No Drawings

PROCESS FOR PRODUCING 1,5-DIAMINONAPHTHALENE

This application is a CON of PCT/JP03/14932 Nov. 21, 2003.

TECHNICAL FIELD

The present invention relates to a process for producing 1,5-diaminonaphthalene. 1,5-Diaminonaphthalene is a useful compound as a raw material for various synthetic resins. In particular, 1,5-naphthalene diisocyanate prepared from 1,5-Diaminonaphthalene is a useful compound as a monomer for polyurethanes having excellent physical properties.

BACKGROUND ART

Conventionally, 1,5-diaminonaphthalene is prepared by converting naphthalene into dinitronaphthalene by dinitration, and then by reducing the nitro groups thereof into amino groups. However, in the dinitration of naphthalene, a large amount of 1,8-dinitronaphthalene is generated as a by-product along with the desired 1,5-dinitronaphthalene. For example, in a method in which naphthalene is nitrated while removing water generated during reaction as an azeotropic mixture by distillation, whereas the yield of 1,5-dinitronaphthalene is 30%, the yield of 1,8-dinitronaphthalene is 65%. That is, the production amount of 1,8-dinitronaphthalene is twice as much as or more than that of 1,5-dinitronaphthalene (Japanese Unexamined Patent Application Publication No. 51-070757). 1,8-dinitronaphthalene is used as a raw material for dyestuffs, etc. Since the production of 1,5-dinitronaphthalene is linked with the production of 1,8-dinitronaphthalene, if the demand for 1,8-dinitronaphthalene is low, it becomes difficult to produce a necessary amount of 1,5-diaminonaphthalene.

In order to overcome such disadvantages, processes are disclosed in which a nitro imine and/or nitro enamine is prepared through two steps using ortho-nitrotoluene and acrylonitrile or the like as starting materials, and the nitro imine and/or nitro enamine is then aromatized and hydrogenated to produce 1,5-diaminonaphthalene (U.S. Patent Application Publication No. 2002/0103401 and PCT Publication No. WO02/090315). However, the nitro imine and nitro enamine, which are the intermediates in such processes, are relatively unstable compounds.

DISCLOSURE OF INVENTION

It is an object of the present invention to provide a novel process for industrially advantageously producing 1,5-diaminonaphthalene without formation of 1,8-diaminonaphthalene which is an isomeric by-product and not through a nitro imine and nitro enamine as intermediates.

As a result of thorough research on the object, the present inventors have found that it is possible to industrially advantageously produce 1,5-diaminonaphthalene from a naphthol compound which is obtained by the aromatization of 5-substituted-1-tetralone and have achieved the present invention. That is, the present invention includes the following Items.

(1) A process for producing 1,5-diaminonaphthalene including the steps of dehydrogenating 5-substituted-1-tetralone to produce a naphthol compound and then aminating the hydroxyl group of the naphthol compound.

(2) A process for producing 1,5-diaminonaphthalene according to Item (1), wherein the substituent in the 5-position of the 5-substituted-1-tetralone is a nitro group or an amino group.

(3) A process for producing 1,5-diaminonaphthalene according to Item (1), wherein 5-nitro-1-tetralone is dehydrogenated and reduced to produce 5-amino-1-naphthol, and then the 5-amino-1-naphthol is aminated.

(4) A process for producing 1,5-diaminonaphthalene according to Item (1), wherein 5-nitro-1-tetralone is dehydrogenated to produce 5-nitro-1-naphthol, the 1-naphthol compound is aminated to produce a 1-naphthylamine compound, and then the 1-naphthylamine compound is reduced.

(5) A process for producing 1,5-diaminonaphthalene according to Item (3), wherein 5-nitro-1-tetralone is dehydrogenated to produce 5-nitro-1-naphthol, the 1-naphthol compound is reduced to produce 5-amino-1-naphthol, and then the 5-amino-1-naphthol is aminated.

(6) A process for producing 1,5-diaminonaphthalene according to Item (3), wherein 5-nitro-1-tetralone is reduced to produce 5-amino-1-tetralone, the 1-tetralone compound is dehydrogenated to produce 5-amino-1-naphthol, and then the 5-amino-1-naphthol is aminated.

BEST MODE FOR CARRYING OUT THE INVENTION

The substituent in the 5-substituted-1-tetralone used in present invention is preferably an amino group or a group convertible into an amino group, and the group convertible into the amino group is preferably a nitro group. Any known method may be employed to prepare 5-substituted-1-tetralone. Examples of methods for preparing 5-nitro-1-tetralone include a method in which α-tetralone is nitrated (German Patent No. 408,665); a method in which 1-nitrotetralin is oxidized by the action of chromium trioxide in acetic acid (German Patent No. 397,150); a method in which ortho-nitrotoluene is reacted with acrylonitrile to prepare 4-(2-nitrophenyl)butyronitrile, the 4-(2-nitrophenyl)butyronitrile is cyclized to prepare a nitro imine and/or nitro enamine (U.S. Patent Application Publication No. 2002/0103401), and the nitro imine and/or nitro enamine is converted into 5-nitro-1-tetralone; and a method in which ortho-nitrotoluene is reacted with an acrylate ester to prepare a 4-(2-nitrophenyl)butanoate ester, and the 4-(2-nitrophenyl)butanoate ester is cyclized (PCT Publication No. WO02/090315). In order to prepare 5-amino-1-tetralone, 5-nitro-1-tetralone is reduced.

A process for producing 1,5-diaminonaphthalene in a first preferred embodiment of the present invention is as follows.

1) By dehydrogenating 5-nitro-1-tetralone, 5-nitro-1-naphthol is produced;

2) by reducing the resultant 5-nitro-1-naphthol, 5-amino-1-naphthol is produced; and 3) by aminating the hydroxyl group of the 5-amino-1-naphthol, 1,5-diaminonaphthalene is produced.

The individual steps will be described below.

[Step 1: Dehydrogenation of 5-nitro-1-tetralone]

In Step 1, 5-nitro-1-tetralone is dehydrogenated to produce 5-nitro-1-naphthol. In this step, any known method for dehydrogenation of alicyclic ketones into phenols may be used. In a typical method, the dehydrogenation is performed by heating 5-nitro-1-tetralone in the presence of a noble metal catalyst. Any noble metal catalyst that is generally used as a hydrogenation catalyst may be used, and examples thereof include Raney metals, such as Raney Ni and Raney Co; and catalysts of the platinum group supported by carriers, such as Pd/C, Pd/alumina, Pt/C, and Pt/alumina. The amount of the catalyst used is 0.001% by weight to about 10% by weight, and preferably 0.01% by weight to 5% by weight, on the basis of the metal, relative to the starting material.

The reaction may be carried out either in a vapor phase or in a liquid phase. Since 5-nitro-1-tetralone has a high boiling point, the reaction in the liquid phase is more advantageous. Examples of solvents used in the liquid phase reaction include water; alcoholic solvents, such as methanol and ethanol; hydrocarbon solvents, such as toluene, xylene, and cyclohexane; ether solvents, such as dioxane and diglyme; ketones, such as methyl ethyl ketone and methyl isobutyl ketone; organic acids, such as acetic acid; and polar solvents, such as N,N-dimethylformamide (hereinafter abbreviated as "DMF"). Above all, solvents which are inactive in the reaction and which dissolve 5-nitro-1-tetralone and the products, i.e., 5-nitro-1-naphthol and 5-amino-1-naphthol, are preferable; hence, ether solvents and polar solvents are preferable. These solvents may be used alone or in combination of two or more. The amount of the solvent used is not particularly limited. In view of the volumetric efficiency and the stirring efficiency, the solvent is used in an amount of 1 to 100 times (by weight) and preferably 1 to 50 times (by weight) the amount of the starting material.

The reaction temperature ranges from room temperature to 300° C., preferably from room temperature to 200° C., and more preferably from room temperature to 130° C. The reaction pressure ranges from atmospheric pressure to 10 MPa, and preferably from atmospheric pressure to 5 MPa.

In the dehydrogenation, 1 mole of hydrogen is stoichiometrically generated for 1 mole of the starting material, so the nitro groups may be reduced to nitroso groups, hydroxylamino groups, or amino groups in some cases to give 5-nitroso-1-naphthol, 5-hydroxylamino-1-naphthol, and 5-amino-1-naphthol in addition to 5-nitro-1-naphthol. However, all of the nitro groups, nitroso groups, and hydroxylamino groups can be converted into amino groups by the reduction in the subsequent step.

[Step 2: Reduction of nitro groups, etc.]

In Step 2, 5-nitro-1-naphthol prepared by the dehydrogenation is reduced to 5-amino-1-naphthol. In this step, any known method for generating amino groups by the reduction of nitro groups may be used. In a typical method, reduction by hydrogen is carried out in the presence of a noble metal catalyst using a solvent. Any noble metal catalyst that is generally used as a hydrogenation catalyst may be used, and the same catalysts as those exemplified in Step 1 may be used. The amount of the catalyst used is 0.001% by weight to about 1% by weight, and preferably 0.01% by weight to 0.5% by weight, on the basis of the metal, relative to the starting material.

As the solvent used in the liquid phase reaction, the same solvents as those exemplified in Step 1 may be used. These solvents may be used alone or in combination of two or more. The amount of the solvent used is not particularly limited. In view of the volumetric efficiency and the stirring efficiency, the solvent is used in an amount of 1 to 100 times (by weight) and preferably 1 to 50 times (by weight) the amount of the starting material.

The reaction temperature ranges from room temperature to 200° C., and preferably from room temperature to 100° C. The reaction pressure ranges from atmospheric pressure to 5 MPa, and preferably from atmospheric pressure to 1 MPa.

Before the reduction is carried out, the product may be isolated from the reaction mass after dehydrogenation. It is, however, industrially advantageous to use the same solvent and the same catalyst in the dehydrogenation step and the reduction step and to carry out the successive reduction by introducing hydrogen into the reactor after the dehydrogenation was carried out.

[Step 3: Amination of 5-amino-1-naphthol]

In Step 3, 5-amino-1-naphthol is aminated to produce 1,5-diaminonaphthalene. The hydroxyl groups are aminated by bringing 5-amino-1-naphthol into contact with ammonia.

Ammonia is used in an amount of 1 to 100 molar times and preferably 1 to 50 molar times the amount of the starting material. The amination can be performed in high yields in the presence of a hydrogensulfite or sulfite aqueous solution. Examples of hydrogensulfites or sulfites include sodium hydrogensulfite, potassium hydrogensulfite, ammonium hydrogensulfite, sodium sulfite, potassium sulfite, and ammonium sulfite. Among them, ammonium hydrogensulfite or ammonium sulfite is preferable. The amination may be performed in the presence of zinc chloride, iodine, calcium chloride, sulfanilic acid, sulfuric acid, or the like. The hydrogensulfite or sulfite is used in an amount of 0.1 to 150 mole percent and preferably 1 to 100 mole percent of the starting material.

The amination is usually carried out in an aqueous solution in a pressure vessel. The reaction may be carried out in a mixed solvent composed of water and a solvent that is miscible with water within the range not to inhibit the reaction. Alternatively, the reaction may be carried out in a two-phase system using water and a solvent that is immiscible with water. Although the amount of the solvent used is not particularly limited, in view of the volumetric efficiency and the stirring efficiency, the solvent is used in an amount of 1 to 100 times (by weight) and preferably 1 to 50 times (by weight) the amount of the starting material.

The reaction temperature ranges from room temperature to 300° C., and preferably from 50° C. to 200° C. The reaction pressure ranges from atmospheric pressure to 10 MPa, and preferably from atmospheric pressure to 5 MPa.

In the process for producing 1,5-diaminonaphthalene in the present invention, 5-nitro-1-tetralone may be reduced in advance to prepare 5-amino-1-tetralone, and then dehydrogenation and amination may be performed. That is, a process for producing 1,5-diaminonaphthalene in a second preferred embodiment of the present invention is as follows.

1) By reducing 5-nitro-1-tetralone, 5-amino-1-tetralone is produced;

2) by dehydrogenating the resultant 5-amino-1-tetralone, 5-amino-1-naphthol is produced; and 3) by aminating the hydroxyl group of the 5-amino-1-naphthol, 1, 5-diaminonaphthalene is produced.

The individual steps will be described below.

[Step 1: Reduction of nitro group]

In Step 1, 5-nitro-1-tetralone is reduced to produce 5-amino-1-tetralone. In this step, any known method for generating amino groups by the reduction of nitro groups may be used. In a typical method, reduction of 5-nitro-1-tetralone is carried out with hydrogen in the presence of a noble metal catalyst using a solvent. Any noble metal catalyst that is generally used as a hydrogenation catalyst may be used, and the same catalysts as those exemplified in Step 1 in the first embodiment may be used. The amount of the catalyst used is 0.001% by weight to about 1% by weight, and preferably 0.01% by weight to 0.5% by weight, on the basis of the metal, relative to the starting material.

The solvents used in this liquid phase reaction may be the same as those exemplified in Step 1 in the first embodiment. These solvents may be used alone or in combination of two or more. The amount of the solvent used is not particularly limited. In view of the volumetric efficiency and the stirring efficiency, the solvent is used in an amount of 1 to 100 times (by weight) and preferably 1 to 50 times (by weight) the amount of the starting material.

The reaction temperature ranges from room temperature to 200° C., and preferably from room temperature to 100° C. The reaction pressure ranges from atmospheric pressure to 5 MPa, and preferably from atmospheric pressure to 1 MPa.

[Step 2: Dehydrogenation of 5-amino-1-tetralone]

In Step 2, 5-amino-1-tetralone is dehydrogenated to produce 5-amino-1-naphthol. In this step, any known method for dehydrogenation of alicyclic ketones into phenols may be used. In a typical method, the dehydrogenation is performed by heating 5-amino-1-tetralone in the presence of a noble metal catalyst.

Any noble metal catalyst that is generally used as a hydrogenation catalyst may be used, and the same catalysts as those exemplified in Step 1 in the first embodiment may be used. The amount of the catalyst used is 0.001% by weight to about 10% by weight, and preferably 0.01% by weight to 5% by weight, on the basis of the metal, relative to the starting material.

The reaction may be carried out either in a vapor phase or in a liquid phase. Since 5-amino-1-tetralone has a high boiling point, the reaction in the liquid phase is more advantageous. The solvents used in the liquid phase reaction may be the same as those exemplified in Step 1 in the first embodiment. Above all, solvents which are inactive in the reaction and which dissolve 5-amino-1-tetralone and that the product 5-amino-1-naphthol are preferable; hence, ether solvents and polar solvents are preferable. These solvents may be used alone or in combination of two or more. The amount of the solvent used is not particularly limited. In view of the volumetric efficiency and the stirring efficiency, the solvent is used in an amount of 1 to 100 times (by weight) and preferably 1 to 50 times (by weight) the amount of the starting material.

The reaction temperature ranges from room temperature to 300° C., preferably from room temperature to 200° C., and more preferably from room temperature to 130° C. The reaction pressure ranges from atmospheric pressure to 10 MPa, and preferably from atmospheric pressure to 5 MPa.

[Step 3: Amination of 5-amino-1-naphthol]

In Step 3, 5-amino-1-naphthol is aminated to produce 1,5-diaminonaphthalene. The hydroxyl groups are aminated by bringing 5-amino-1-naphthol into contact with ammonia. Ammonia is used in an amount of 1 to 100 molar times and preferably 1 to 50 molar times the amount of the starting material. The amination can be performed in high yields in the presence of a hydrogensulfite or sulfite aqueous solution. The same hydrogensulfites or sulfites as those exemplified in Step 3 in the first embodiment may be used. The amination may be performed in the presence of zinc chloride, iodine, calcium chloride, sulfanilic acid, sulfuric acid, or the like. The hydrogensulfite or sulfite is used in an amount of 0.1 to 150 mole percent and preferably 1 to 100 mole percent of the starting material.

The reaction is usually carried out in an aqueous solution in a pressure vessel. The reaction may be carried out in a mixed solvent composed of water and a solvent that is miscible with water within the range not to inhibit the reaction. Alternatively, the reaction may be carried out in a two-phase system using water and a solvent that is immiscible with water. Although the amount of the solvent used is not particularly limited, in view of the volumetric efficiency and the stirring efficiency, the solvent is used in an amount of 1 to 100 times (by weight) and preferably 1 to 50 times (by weight) the amount of the starting material.

The reaction temperature ranges from room temperature to 300° C., and preferably from 50° C. to 200° C. The reaction pressure ranges from atmospheric pressure to 10 MPa, and preferably from atmospheric pressure to 5 MPa.

In the process for producing 1,5-diaminonaphthalene in the present invention, 5-nitro-1-tetralone may be dehydrogenated and aminated to produce 5-nitro-1-naphthylamine, and then the nitro groups may be reduced. That is, a process for producing 1,5-diaminonaphthalene in a third preferred embodiment of the present invention is as follows.

1) By dehydrogenating 5-nitro-1-tetralone, 5-nitro-1-naphthol is produced;

2) by aminating the hydroxyl group of the resultant 5-nitro-1-naphthol, 5-nitro-1-naphthylamine is produced; and 3) By reducing 5-nitro-1-naphthylamine, 1,5-diaminonaphthalene is produced.

The individual steps will be described below.

[Step 1: Dehydrogenation of 5-nitro-1-tetralone]

The dehydrogenation can be performed as in Step 1 in the first embodiment. In this reaction, 5-nitroso-1-naphthol, 5-hydroxylamino-1-naphthol, and 5-amino-1-naphthol may also be formed in addition to 5-nitro-1-naphthol. However, since the nitro groups, nitroso groups, and hydroxylamino groups can be converted into amino groups by the reduction in Step 3, all of the compounds can be used in the amination reaction in Step 2.

[Step 2: Amination reaction of 5-nitro-1-naphthol]

In Step 2, 5-nitro-1-naphthol is aminated to produce 5-nitro-1-naphthylamine. The hydroxyl groups are aminated by bringing 5-nitro-1-naphthol into contact with ammonia. Ammonia is used in an amount of 1 to 100 molar times and preferably 1 to 50 molar times the amount of the starting material. The amination can be performed in high yields in the presence of a hydrogensulfite or sulfite aqueous solution. The same hydrogensulfites or sulfites as those exemplified in Step 3 in the first embodiment may be used. The amination may be performed in the presence of zinc chloride, iodine, calcium chloride, sulfanilic acid, sulfuric acid, or the like. The hydrogensulfite or sulfite is used in an amount of 0.1 to 150 mole percent and preferably 1 to 100 mole percent of the starting material.

The reaction is usually carried out in an aqueous solution in a pressure vessel. The reaction may be carried out in a mixed solvent composed of water and a solvent that is miscible with water within the range not to inhibit the reaction. Alternatively, the reaction may be carried out in a two-phase system using water and a solvent that is immiscible with water. Although the amount of the solvent used is not particularly limited, in view of the volumetric efficiency and the stirring efficiency, the solvent is used in an amount of 1 to 100 times (by weight) and preferably 1 to 50 times (by weight) the amount of the starting material.

The reaction temperature ranges from room temperature to 300° C., and preferably from 50° C. to 200° C. The reaction pressure ranges from atmospheric pressure to 10 MPa, and preferably from atmospheric pressure to 5 MPa.

[Step 3: Reduction of nitro group, etc.]

In Step 3, the 5-nitro-1-naphthylamine obtained by the amination reaction is reduced to produce 1,5-diaminonaphthalene. In this step, any known method for generating amino groups by the reduction of nitro groups may be used. In a typical method, reduction of 5-nitro-1-naphthylamine is carried out with hydrogen in the presence of a noble metal catalyst using a solvent. Any noble metal catalyst that is generally used as a hydrogenation catalyst may be used, and the same catalysts as those exemplified in Step 1 in the first embodiment may be used. The amount of the catalyst used is 0.001% by weight to about 1% by weight, and preferably 0.01% by weight to 0.5% by weight, on the basis of the metal, relative to the starting material.

As the solvent used in the liquid phase reaction, the same solvents as those exemplified in Step 1 in the first embodiment may be used. These solvents may be used alone or in combination of two or more. The amount of the solvent used is not particularly limited. In view of the volumetric efficiency and the stirring efficiency, the solvent is used in an amount of 1 to 100 times (by weight) and preferably 1 to 50 times (by weight) the amount of the starting material.

The reaction temperature ranges from room temperature to 200° C., and preferably from room temperature to 100° C. The reaction pressure ranges from atmospheric pressure to 5 MPa, and preferably from atmospheric pressure to 1 MPa.

The present invention will be described in detail based on the examples below. However, it is to be understood that the present invention is not limited thereto.

EXAMPLE 1
Dehydrogenation of 5-nitro-1-tetralone

In a four-necked flask was placed 10.0 g of 5-nitro-1-tetralone, 4.0 g of 5% Pd/C (containing 50% by weight of water), and 50.0 g of DMF, and the reaction was carried out at 130° C. for 24 hours while the reaction mixture was bubbled with nitrogen at 0.6 L/min. After the reaction mixture was cooled, the catalyst was filtered off, and washed with DMF. The reaction mass thus obtained was analyzed by gas chromatography. As a result, the remaining content of 5-nitro-1-tetralone, i.e., the starting material, was 3.3%; the yield of 5-amino-1-tetralone was 3.6% (conversion 93.1% as tetralones); the yield of 5-nitro-1-naphthol was 47.0%; and the yield of 5-amino-1-naphthol was 21.4% (selectivity 73.5% as naphthols).

Gas chromatography analysis conditions
Capillary column: DB-1 (manufactured by J & W Corp.), inside diameter 0.53 mm, length 30 m
Column temperature: 200° C.
Injection temperature: 320° C.
Detector temperature: 320° C.

EXAMPLE 2
Dehydrogenation of 5-nitro-1-tetralone

In an autoclave was placed 10.0 g of 5-nitro-1-tetralone, 4.0 g of 5% Pd/C (containing 50% by weight of water), and 50.0 g of diglyme, and the reaction was carried out at 130° C. for 18 hours. After the reaction mixture was cooled, the catalyst was filtered off, and washed with diglyme. The reaction mass thus obtained was analyzed by gas chromatography. As a result, the remaining content of 5-nitro-1-tetralone, i.e., the starting material, was 13.3%; the yield of 5-amino-1-tetralone was 2.6% (conversion 84.1% as tetralones); the yield of 5-nitro-1-naphthol was 51.9%; and the yield of 5-amino-1-naphthol was 21.2% (selectivity 86.9% as naphthols).

EXAMPLE 3
Dehydrogenation of 5-nitro-1-tetralone

In an autoclave was placed 10.0 g of 5-nitro-1-tetralone, 4.0 g of 5% Pd/C (containing 50% by weight of water), and 50.0 g of isopropanol, and the reaction was carried out at 130° C. for 12 hours. After the reaction mixture was cooled, the catalyst was filtered off, and washed with diglyme. The reaction mass thus obtained was analyzed by gas chromatography. As a result, the remaining content of 5-nitro-1-tetralone, i.e., the starting material, was 43.5%; the yield of 5-amino-1-tetralone was 12.0% (conversion 44.5% as tetralones); the yield of 5-nitro-1-naphthol was 17.7%; and the yield of 5-amino-1-naphthol was 7.1% (selectivity 55.7% as naphthols).

EXAMPLE 4
Dehydrogenation of 5-nitro-1-tetralone

In an autoclave was placed 10.0 g of 5-nitro-1-tetralone, 4.0 g of 5% Pd/C (containing 50% by weight of water), and 50.0 g of toluene, and the reaction was carried out at 130° C. for 12 hours. After the reaction mixture was cooled, the catalyst was filtered off, and washed with diglyme. The reaction mass thus obtained was analyzed by gas chromatography. As a result, the remaining content of 5-nitro-1-tetralone, i.e., the starting material, was 73.1%; the yield of 5-amino-1-tetralone was 2.4% (conversion 24.5% as tetralones); the yield of 5-nitro-1-naphthol was 6.7%; and the yield of 5-amino-1-naphthol was 1.6% (selectivity 33.9% as naphthols).

EXAMPLE 5
Dehydrogenation of 5-nitro-1-tetralone

In an autoclave was placed 10.0 g of 5-nitro-1-tetralone, 4.0 g of 5% Pd/C (containing 50% by weight of water), and 50.0 g of methyl isobutyl ketone, and the reaction was carried out at 130° C. for 12 hours. After the reaction mixture was cooled, the catalyst was filtered off, and washed with diglyme. The reaction mass thus obtained was analyzed by gas chromatography. As a result, the remaining content of 5-nitro-1-tetralone, i.e., the starting material, was 73.8%; the yield of 5-amino-1-tetralone was 2.6% (conversion 23.6% as tetralones); the yield of 5-nitro-1-naphthol was 11.8%; and the yield of 5-amino-1-naphthol was 1.9% (selectivity 58.1% as naphthols).

EXAMPLE 6
Dehydrogenation of 5-nitro-1-tetralone

In an autoclave was placed 10.0 g of 5-nitro-1-tetralone, 4.0 g of 5% Pd/C (containing 50% by weight of water), and 50.0 g of acetic acid, and the reaction was carried out at 130° C. for 12 hours. After the reaction mixture was cooled, the catalyst was filtered off, and washed with diglyme. The reaction mass thus obtained was analyzed by gas chromatography. As a result, the remaining content of 5-nitro-1-tetralone, i.e., the starting material, was 30.6%; the yield of 5-amino-1-tetralone was 0.6% (conversion 68.8% as tetralones); the yield of 5-nitro-1-naphthol was 39.0%; and the yield of 5-amino-1-naphthol was 0.6% (selectivity 57.6% as naphthols).

EXAMPLE 7
Reduction of 5-nitro-1-naphthol

In an autoclave was placed 1.9 g of 5-nitro-1-naphthol, 0.02 g of 5% Pd/C (containing 50% by weight of water), and 50 g of isopropanol, and the hydrogen pressure was set at 0.8 MPa. The reaction was carried out at 50° C. for 2 hours. After the reaction mixture was cooled, the catalyst was filtered off, and the reaction mass thus obtained was analyzed by gas chromatography. As a result, the content of 5-amino-1-naphthol produced was 1.5 g (yield 95%).

EXAMPLE 8
Amination of 5-amino-1-naphthol

In an autoclave was placed 8.0 g (0.05 moles) of 5-amino-1-naphthol, 10.2 g of 50% ammonium hydrogensulfite aqueous solution, 30.4 g of 28% aqueous ammonia (0.5 moles of ammonia), and 25.0 g of water, and the reaction was carried out at 150° C. for 6 hours. After the reaction mixture was cooled, the contents were dissolved in DMF. Quantification by HPLC indicated that the remaining content of 5-amino-1-naphthol, i.e., the starting material, was 4.4% and the yield of 1,5-diaminonaphthalene was 93.0% (selectivity 97.3%).

HPLC conditions

Column: YMC-312A (ODS) (manufactured by YMC Corp.)

Eluent: water:methanol:PIC=900:2,100:9 (volume ratio)

PIC=tetra-n-butylammonium hydroxide (10% in methanol)

Flow rate: 1 ml/min

Detection wavelength: 254 nm

EXAMPLE 9

Amination of 5-amino-1-naphthol

In an autoclave was placed 8.0 g (0.05 moles) of 5-amino-1-naphthol, 10.2 g of 50% ammoniumhydrogensulfite aqueous solution, 30.4 g of 28% aqueous ammonia (0.5 moles of ammonia), and 25.0 g of diglyme, and the reaction was carried out at 150° C. for 6 hours. After the reaction mixture was cooled, the contents were dissolved in DMF. Quantification by HPLC indicated that the remaining content of 5-amino-1-naphthol, i.e., the starting material, was 6.2% and the yield of 1,5-diaminonaphthalene was 93.6% (selectivity 99.8%).

Industrial Applicability

According to the process of the present invention, it is possible to produce 1,5-diaminonaphthalene, which is a raw material for 1,5-naphthalene diisocyanate, etc., without the formation of positional isomers. 1,5-Naphthalene diisocyanate is a useful compound as a monomer for polyurethanes.

What is claimed is:

1. A process for producing 1,5-diaminonaphthalene comprising the steps of dehydrogenating 5-substituted-1-tetralone to produce a naphthol compound and then aminating the hydroxyl group of the naphthol compound.

2. A process for producing 1,5-diaminonaphthalene according to claim 1, wherein the substituent in the 5-position of the 5-substituted-1-tetralone is a nitro group or an amino group.

3. A process for producing 1,5-diaminonaphthalene according to claim 1, wherein 5-nitro-1-tetralone is dehydrogenated and reduced to produce 5-amino-1-naphthol, and then the 5-amino-1-naphthol is aminated.

4. A process for producing 1,5-diaminonaphthalene according to claim 1, wherein 5-nitro-1-tetralone is dehydrogenated to produce 5-nitro-1-naphthol, the 1-naphthol compound is aminated to produce a 1-naphthylamine compound, and then the 1-naphthylamine compound is reduced.

5. A process for producing 1,5-diaminonaphthalene according to claim 3, wherein 5-nitro-1-tetralone is dehydrogenated to produce 5-nitro-1-naphthol, the 1-naphthol compound is reduced to produce 5-amino-1-naphthol, and then the 5-amino-1-naphthol is aminated.

6. A process for producing 1,5-diaminonaphthalene according to claim 3, wherein 5-nitro-1-tetralone is reduced to produce 5-amino-1-tetralone, the 1-tetralone compound is dehydrogenated to produce 5-amino-1-naphthol, and then the 5-amino-1-naphthol is aminated.

* * * * *